(12) United States Patent
Geisz et al.

(10) Patent No.: US 11,957,830 B2
(45) Date of Patent: Apr. 16, 2024

(54) METHOD AND SYSTEM FOR DELIVERING INSUFFLATION FLUID

(71) Applicant: Lexion Medical, LLC, St. Paul, MN (US)

(72) Inventors: Carl M. Geisz, Edina, MN (US); Rochelle M. Amann, Mendola Heights, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 1021 days.

(21) Appl. No.: 16/592,358

(22) Filed: Oct. 3, 2019

(65) Prior Publication Data

US 2021/0100964 A1 Apr. 8, 2021

(51) Int. Cl.
*A61M 13/00* (2006.01)
*A61B 17/00* (2006.01)
(Continued)

(52) U.S. Cl.
CPC ....... *A61M 13/003* (2013.01); *A61B 17/3423* (2013.01); *A61B 17/3474* (2013.01); *A61B 34/30* (2016.02); *A61M 39/24* (2013.01); *A61B 2017/00477* (2013.01); *A61B 2034/302* (2016.02); *A61M 2039/0264* (2013.01); (Continued)

(58) Field of Classification Search
CPC .............. A61M 13/003; A61M 39/24; A61M 2039/0264; A61M 2039/0276; A61M 2039/0279; A61M 2205/3344; A61M 2205/36; A61M 39/0247; A61M 2039/0267; A61M 2039/027; A61M 2039/0646; A61M 13/00; A61M 13/006; A61B 17/3423; A61B 17/3474; A61B 34/30; A61B 2017/00477; A61B 2034/302; A61B 17/3417; A61B 17/3421; A61B 17/3462; A61B 17/34; A61B 17/3415; A61B 2017/3419; A61B 2017/3427;
(Continued)

(56) References Cited

U.S. PATENT DOCUMENTS

| 9,381,312 B1 * | 7/2016 | Ott ..................... A61B 17/3474 |
| 2007/0088275 A1 * | 4/2007 | Stearns ............... A61M 13/003 604/164.01 |

(Continued)

OTHER PUBLICATIONS

"DaVinciXi Introduction Engadget" YouTube Video, https://www.youtube.com/watch?v=_q-VQwFjlj0, Engadget, Published Apr. 3, 2014.

(Continued)

*Primary Examiner* — Ariana Zimbouski
*Assistant Examiner* — Avery Smale
(74) *Attorney, Agent, or Firm* — Baker Botts L.L.P.

(57) ABSTRACT

A method for supplying insufflation fluid to a patient cavity includes positioning a secondary trocar at least partially within a primary trocar, the secondary trocar being configured to facilitate delivery of insufflation fluid to a patient cavity. The method further includes, upon positioning the secondary trocar at least partially within the primary trocar, coupling the secondary trocar to the primary trocar thereby forming a trocar assembly. The method further includes coupling the primary trocar to a surgical robot and delivering the insufflation fluid to the patient cavity using the trocar assembly.

12 Claims, 6 Drawing Sheets

(51) Int. Cl.
*A61B 17/34* (2006.01)
*A61B 34/30* (2016.01)
*A61M 39/02* (2006.01)
*A61M 39/24* (2006.01)

(52) U.S. Cl.
CPC ............... *A61M 2039/0276* (2013.01); *A61M 2039/0279* (2013.01); *A61M 2205/3344* (2013.01)

(58) Field of Classification Search
CPC ...... A61B 2017/3445; A61B 2017/347; A61B 17/3498
See application file for complete search history.

(56) References Cited

U.S. PATENT DOCUMENTS

| | | | |
|---|---|---|---|
| 2011/0046449 A1* | 2/2011 | Minnelli ............ | A61B 1/00137 600/210 |
| 2015/0290403 A1* | 10/2015 | Torisawa ............ | A61B 17/3474 604/26 |
| 2017/0281286 A1* | 10/2017 | Braun ................ | A61B 17/3462 |
| 2018/0008313 A1* | 1/2018 | Augelli ............. | A61B 17/3417 |
| 2018/0103977 A1* | 4/2018 | Geisz ............... | A61B 17/00234 |
| 2018/0344952 A1 | 12/2018 | Geisz et al. | |
| 2020/0187984 A1* | 6/2020 | Silver ............... | A61B 17/3423 |

OTHER PUBLICATIONS

"DavinciXi Instruments and Docking" YouTube Video, https://www.youtube.com/watch?v=BMIoAr0LYS4, Engadget, Published Jul. 15, 2017.

* cited by examiner

METHOD AND SYSTEM FOR DELIVERING INSUFFLATION FLUID

TECHNICAL FIELD

The present disclosure relates generally to medical procedures and more particularly to a method and system for delivering insufflation fluid to a body cavity.

BACKGROUND

A number of patient surgeries are now being performed with robotic assistance. The benefits of robotic-assisted surgery are many. For example, by employing robotic systems during surgery, surgeons may experience better visualization, dexterity, precision and comfort relative to performing conventional, non-robot assisted surgery. The benefits of robotic-assisted surgery also extend to the patients undergoing the surgery. As an example, patients may experience fewer complications after undergoing robotic-assisted surgery as compared to patients who did not have robot-assisted surgery.

Irrespective of whether a surgery is being performed with the assistance of a robot, it is commonplace for surgeons to insufflate a body cavity when performing surgeries. Generally, insufflation refers to the act of blowing a substance (e.g., gas, powder, vapor) into a body cavity. Introduction of an insufflation substance into a body cavity results in the inflation or distention of the cavity such as to (1) allow the surgeon to explore the area in which the surgery will be performed and (2) provide a view of the site to be treated or observed.

SUMMARY

According to one embodiment, a system includes a primary trocar and a secondary trocar. The primary trocar includes a lip, a single lumen, and a docking mount. The docking mount is configured to engage with a robotic arm of a surgical robot. The secondary trocar is configured to be positioned at least partially within the primary trocar and is further configured to facilitate delivery of insufflation fluid to a patient cavity. The secondary trocar includes a trocar head, a double lumen, and one or more conditioning elements. The trocar head includes one or more latches configured to engage the lip of the primary trocar to facilitate coupling of the primary trocar and the secondary trocar. The double lumen includes an outer lumen disposed about an inner lumen, the outer lumen includes at least one sensor and one or more openings. The at least one sensor is configured to determine a pressure measurement indicative of a pressure of the patient cavity and the one or more openings are configured to direct the insufflation fluid into the patient cavity. The one or more conditioning elements are configured to heat and/or humidify the insufflation fluid. When the primary trocar and the secondary trocar are coupled: a fluid seal exists between the primary trocar and the secondary trocar, the fluid seal being provided at least partially by a gasket; the one or more openings in the outer lumen of the secondary trocar extend beyond the single lumen of the primary trocar; and the insufflation fluid is supplied based on the pressure measurement.

According to another embodiment, a system includes a primary trocar and a secondary trocar. The primary trocar includes a lip, a single lumen, and a docking mount. The docking mount is configured to engage with a robotic arm of a surgical robot. The secondary trocar is configured to be positioned at least partially within the primary trocar and being further configured to facilitate delivery of insufflation fluid to a patient cavity. The secondary trocar includes a trocar head and a double lumen. The double lumen includes an outer lumen disposed about an inner lumen, the outer lumen including one or more openings configured to direct the insufflation fluid into the patient cavity. The primary trocar and the secondary trocar are further configured to be coupled together and, when coupled: a fluid seal exists between the primary trocar and the secondary trocar and the one or more openings in the outer lumen of the secondary trocar extend beyond the single lumen of the primary trocar.

According to yet another embodiment, a method for supplying insufflation fluid to a patient cavity includes positioning a secondary trocar at least partially within a primary trocar and, upon positioning the secondary trocar at least partially within the primary trocar, coupling the secondary trocar to the primary trocar thereby forming a trocar assembly. The secondary trocar is configured to facilitate delivery of insufflation fluid to a patient cavity and, when the primary trocar and secondary trocar are coupled, one or more openings in an outer lumen of the secondary trocar extend beyond a single lumen of the secondary trocar and a fluid seal is created between the primary trocar and secondary trocar. The method further includes coupling the primary trocar to a surgical robot and delivering the insufflation fluid to the patient cavity using the trocar assembly.

The teachings of the disclosure provide one or more technical advantages. Embodiments of the disclosure may have none, some, or all of these advantages. For example, the systems and methods described herein may permit insufflation fluid to be delivered to a patient cavity through a robotically-controlled trocar. By delivering insufflation via a robotically-controlled trocar, surgeons may reduce the number of incisions made to a patient, thereby simplifying patient recovery and reducing the risk of surgical complications as compared to conventional means of delivering insufflation fluid (e.g., via a separate trocar at a separate surgical site while performing robotic-assisted surgery at a site of interest). As another example, insufflation fluid may be delivered to a patient cavity, via a robotically-controlled trocar, at a constant, predictable flow. As will described in further detail below, certain embodiments disclosed herein provide an insufflation fluid flow path that is undisturbed by the introduction or removal of medical instruments to or from, respectively, the robotically-controlled trocar. Yet another advantage of the systems and methods recited herein is the delivery of conditioned (i.e., heated and/or humidified) insufflation fluid to a body cavity through a robotically-controlled trocar. Clinical benefits such as reduced instances of hypothermia, reduced instances of peritoneal damage, reduced instances of post-operative pain, and shortened recovery time may result from delivering conditioned insufflation fluid to a patient cavity during surgery (e.g., laproscopic surgery). As yet another example, one or more embodiments of the systems and methods disclosed herein provide for more accurate assessment of the pressure in a patient cavity due in part to the proximity of the pressure sensor to the patient cavity. Also, it is out of the gas flow stream which can create inaccurate pressure readings. Other advantages will be apparent to those of skill in the art.

BRIEF DESCRIPTION OF THE DRAWINGS

For a more complete understanding of embodiments of the disclosure and the potential advantages thereof, reference is now made to the following written description taken in conjunction with the accompanying drawings, in which.

DETAILED DESCRIPTION OF THE DRAWINGS

The teachings of certain portions of the present disclosure recognize certain benefits of employing a trocar assembly comprising a primary trocar and a secondary trocar during robotic-assisted surgery. As will be described in further detail below, the secondary trocar of the trocar assembly may employ various components that permit insufflation fluid to be delivered to a patient cavity more effectively than conventional systems and methods that do not utilize the described trocar assembly. Example embodiments are best understood by referring to FIGS. 1 through 5 of the drawings and the description below, like numerals being used for like and corresponding parts of the various drawings.

Figure 1A:
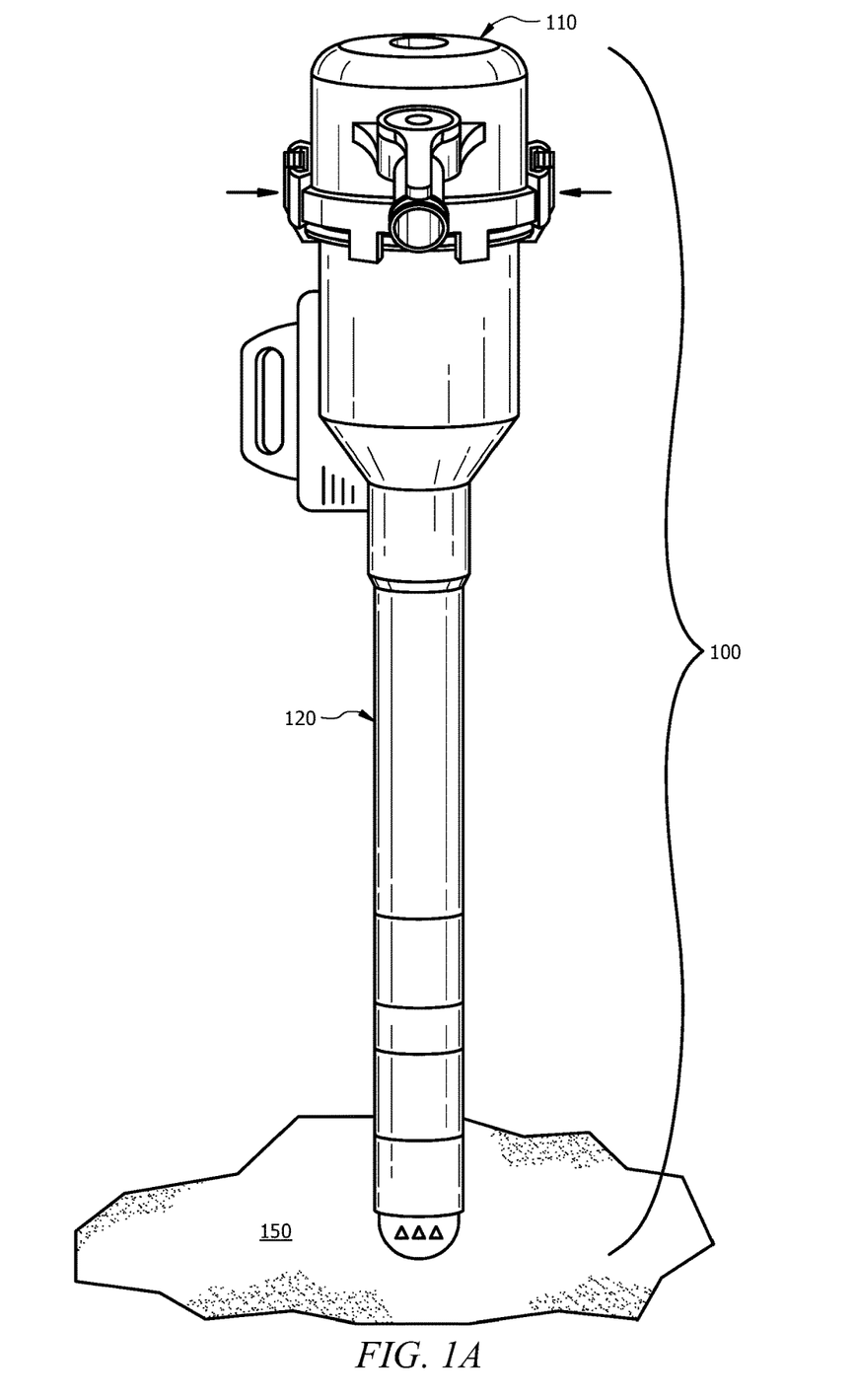
FIG. 1A is a schematic diagram illustrating a trocar assembly comprising a primary trocar and a secondary trocar, according to certain embodiments.

FIG. 1A is a schematic diagram illustrating one embodiment of a trocar assembly 100. Trocar assembly 100 is configured to be maneuvered by a surgical robot. Generally, trocar assembly 100 permits insufflation fluid to be delivered to a patient cavity 150 at a predictable and steady rate without having to make and deliver insufflation fluid through a separate incision site. In some embodiments, trocar assembly 100 delivers conditioned insufflation fluid to patient cavity 150.

As illustrated in FIG. 1A, trocar assembly 100 includes a primary trocar 120 and a secondary trocar 110. Primary trocar 120 is configured to couple to a surgical robot. In some embodiments, a coupling mechanism (e.g., docking mount 430 of FIG. 3) on primary trocar 120 serves as an attachment point to couple trocar assembly 100 to a surgical robot.

Figure 1B:
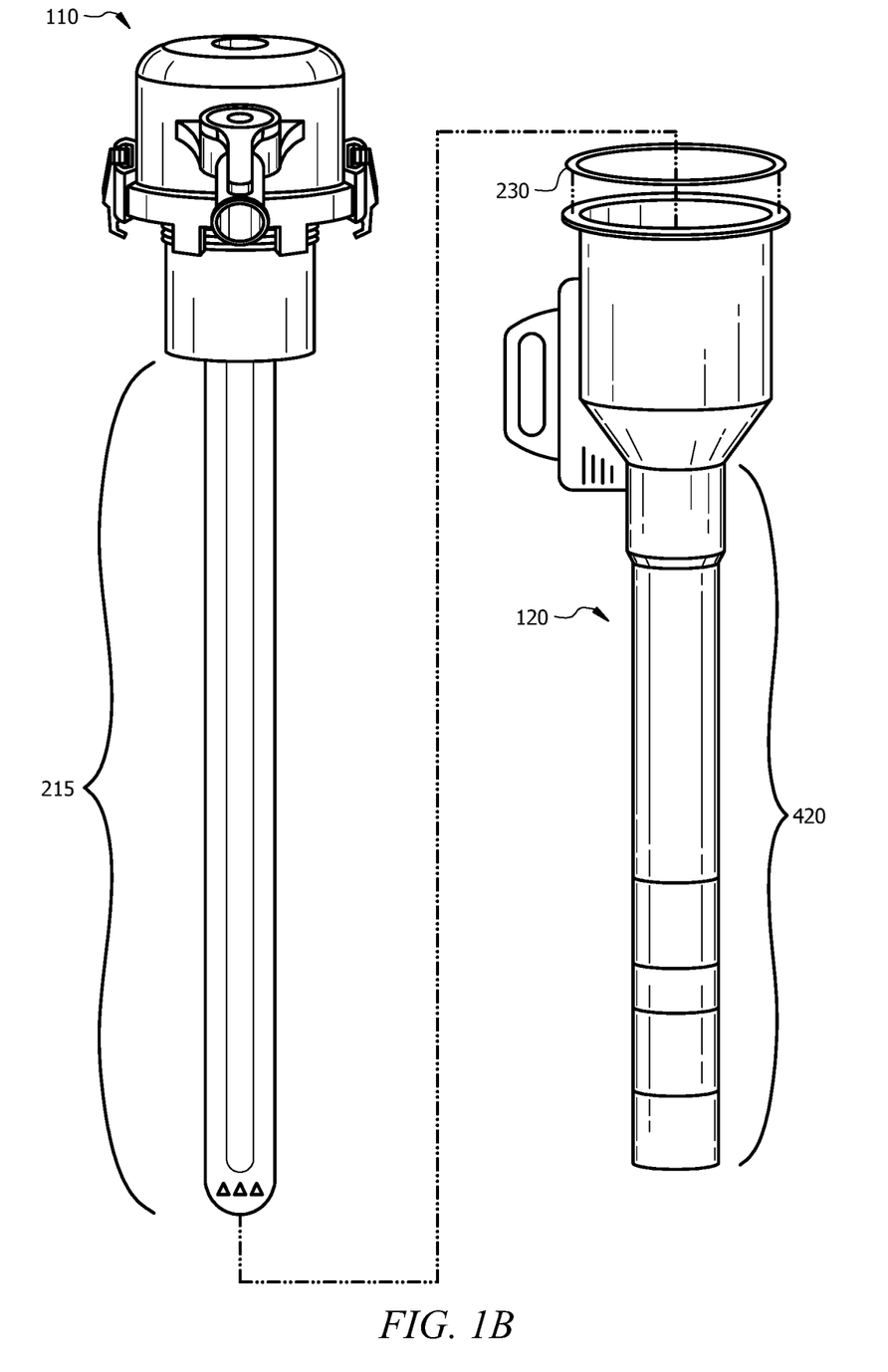
FIG. 1B is a schematic diagram illustrating how to assemble the trocar assembly of FIG. 1, according to certain embodiments.

Secondary trocar 110 may be configured such that it can be at least partially positioned within primary trocar 120. Accordingly, secondary trocar 110 (or portions thereof) is sized to fit within primary trocar 120. For example, the diameter of a cannula (cannula 215 shown in FIG. 1B) of secondary trocar 110 is less than the diameter of a cannula (cannula 420 shown in FIG. 1B) of primary trocar 120. FIG. 1B illustrates how trocar assembly 100 is assembled, according to certain embodiments. Additional details regarding secondary trocar 110 and primary trocar 120 are provided below in reference to FIGS. 2-3 and FIG. 4, respectively. Finally, FIG. 5 describes and illustrates a particular method of delivering insufflation fluid to patient cavity 150 using trocar assembly 100.

Trocar assembly 100 may be formed or otherwise assembled by inserting at least a portion of secondary trocar 110 into and/or through primary trocar 120. As illustrated in FIG. 1B, a distal tip of secondary trocar 110 (i.e., the end of cannula 215 comprising apertures 225) can be inserted through a proximal end of primary trocar 120 (i.e., the mouth of chamber 340 of primary trocar 120) such that cannula 215 of secondary trocar 110 extends through cannula 420 of primary trocar 120. In some embodiments, cannula 215 of secondary trocar 110 extends beyond the distal end of cannula 420 such that apertures 225 are not covered by cannula 420. As will be described in further detail below, primary trocar 120 and secondary trocar 110 may be coupled in a way that permits the creation of a fluid seal between them.

Figure 2:
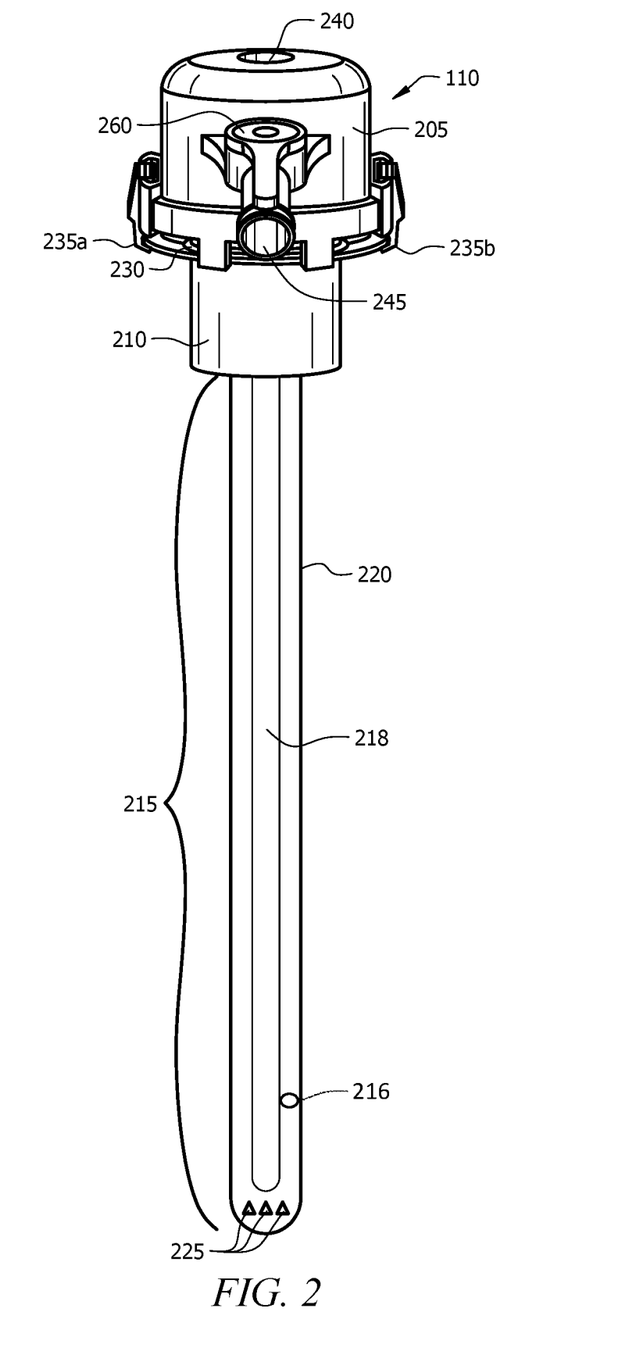
FIG. 2 is a schematic diagram of the secondary trocar of FIG. 1, according to certain embodiments.

FIG. 2 illustrates one embodiment of secondary trocar 110. As described above, secondary trocar may include one or more components that facilitate the delivery of insufflation fluid to patient cavity 150 more effectively than conventional means of doing so. As illustrated in FIG. 2, secondary trocar 110 includes a trocar head 205, a chamber 210, cannula 215, and a gasket 230. In some embodiments, cannula 215 includes an inner lumen 218 and an outer lumen 220. As will be described below, inner lumen 218 may be sized to accommodate one or more medical instruments and outer lumen 220 may provide a flow path for insufflation fluid.

Generally, trocar head 205 is configured to receive insufflation fluid from an insufflator and direct the insufflation fluid to cannula 215 of secondary trocar 110. In some particular embodiments, trocar head 205 is configured such that insufflation fluid is directed from trocar head 205 to a particular lumen (e.g., outer lumen 220) of cannula 215.

As illustrated in FIG. 2, trocar head 205 includes an opening 240. Opening 240 is configured to accommodate at least one medical instrument. In some embodiments, opening 240 provides access therethrough to cannula 215. In some particular embodiments, opening 240 provides access to a particular lumen (e.g., inner lumen 218) of cannula 215. As will be understood by one of ordinary skill, technical benefits may be achieved by separating the instrument path through trocar assembly from the insufflation flow path through trocar assembly. For example, by directing insufflation fluid through outer lumen 220 of cannula 215 and directing one or more medical instruments through inner lumen 218, the one or more medical instruments do not interrupt or otherwise agitate the flow of insufflation fluid into patient cavity 150. As such, insufflation fluid can be delivered to patient cavity 150 at a predictable and steady rate, thereby keeping the cavity distended permitting better site access and visibility for surgeons.

As described above, secondary trocar 110 is configured to couple to primary trocar 120. In some embodiments, secondary trocar 110 couples to primary trocar 120 in a manner that creates a fluid seal. A fluid seal may be created between primary trocar 120 and secondary trocar 110 in any suitable manner. In the embodiment illustrated in FIG. 2, a fluid seal is created using gasket 230 and coupling mechanisms 235. As illustrated in FIG. 2, primary trocar 120 includes two coupling mechanisms 235a and 235b positioned about trocar head 205. Each coupling mechanism 235 is configured to engage with a portion of primary trocar 120 (e.g., lip 410 of primary trocar 120), thereby securing secondary trocar 110 to primary trocar 120. To couple secondary trocar 110 to primary trocar 120, secondary trocar 110 may be positioned at least partially within primary trocar 120 (e.g., such that cannula 214 of secondary trocar 110 extends through cannula 420 of primary trocar 120 and/or trocar head 205 of secondary trocar 110 rests atop lip 410 of primary trocar 120). Although this disclosure depicts coupling mechanism 235 as one or more latches, this disclosure recognizes that coupling mechanism 235 may be any suitable component(s) that permits the coupling of secondary trocar 110 to primary trocar 120.

Although depicted as being a subcomponent of secondary trocar 110, gasket 230 may generally be a subcomponent of trocar assembly 100 (e.g., such that gasket 230 can be added or removed to secondary trocar 110 as desired). Generally, gasket 230 is configured to create a fluid seal between secondary trocar 110 and primary trocar 120. In effect, the fluid seal prevents or otherwise reduces the loss of substances (e.g., insufflation gas, hydration gas) from trocar assembly 100. In some embodiments, a fluid seal is created when secondary trocar 110 and primary trocar 120 are coupled (e.g., using coupling mechanism 235). Gasket 230 may seal secondary trocar 110 to primary trocar 120 in any suitable way. As one example, sealing may occur by compressing gasket 230 such that zero clearance results between secondary trocar 110 and primary trocar 120.

As will be recognized by one of ordinary skill, there are a number of ways to create a fluid seal between two mating parts. This disclosure contemplates using any suitable means to create the fluid seal. For example, trocar head 205 and primary trocar 110 may each include a flange (e.g., lip 410 of primary trocar) that facilitate compression of a sealing element upon tightening of a flange joint. As another example, primary trocar 110 and secondary trocar 120 may be coupled by implementing a press fit (also known as a friction fit) assembly.

Chamber 210 of secondary trocar may be configured, or otherwise adapted, to fit at least partially within chamber 340 of primary trocar. In some embodiments, chamber 210 includes one or more conditioning elements configured to heat and/or humidify insufflation fluid being directed from trocar head 205 to cannula 215. As an example, chamber 210 may include one or more heating and/or humidifying elements as described in U.S. application Ser. No. 13/065,438, filed on Mar. 22, 2011, and entitled "Insufflation Apparatus," which is incorporated by reference herein. For the avoidance of doubt, this disclosure also recognizes that one or more conditioning elements (such as those described in described in U.S. application Ser. No. 13/065,438) may be located in trocar head 205 rather than chamber 210.

Secondary trocar 110 may also include one or more intake ports 245. As used herein, "intake port" refers to any termination of secondary trocar 110 configured to be an entry point for substances (e.g., liquids, gases, powders). In some embodiments, such as the embodiments illustrated in FIGS. 3A & 3B, intake ports 245 are located on trocar head 205. Intake ports 245 may be configured to couple to conduits configured to transport substances to trocar assembly 100. In some embodiments, a diameter of the one or more conduits is larger than the diameter of the one or more intake ports 245 such that coupling requires insertion of intake ports 245 into conduits. In other embodiments, a diameter of the one or more intake ports 245 is larger than the diameter of the one or more conduits such that coupling requires insertion of conduits into intake ports 245. Although this disclosure describes particular ways of coupling intake ports 245 to conduits, this disclosure recognizes any suitable method of coupling intake ports 245 to conduits.

As described above, cannula 215 may include an inner lumen 218 and an outer lumen 220. Outer lumen 220 may be disposed about inner lumen 218. In some embodiments, inner lumen 218 and outer lumen 220 are the same length. In other embodiments, inner lumen 218 and outer lumen 220 are different lengths.

Inner lumen 218 may be sized to accommodate one or more medical instruments therethrough. In some embodiments, inner lumen 218 is substantially separated from outer lumen 220 (e.g., by walls defining inner lumen 218) as to ensure that insertion and movement of a medical instrument within inner lumen 218 has little to no effect on the flow of insufflation gas into patient cavity 150.

In some embodiments, outer lumen 220 defines a portion of a delivery path for insufflation fluid. Outer lumen 220 may receive insufflation fluid delivered to one or more intake ports 245 and direct the insufflation fluid to patient cavity 150. Insufflation fluid may be introduced to a patient cavity 150 by way of one or more apertures 225 directing insufflation fluid into patient cavity 150. In some embodiments, when primary trocar 120 and secondary trocar 110 are coupled together, cannula 215 of secondary trocar 110 extends beyond the distal tip of cannula 420 of primary trocar such that apertures 225 of cannula 215 are not sheathed by cannula 420. By exposing apertures 225 to body cavity 150 (rather than sheathing over them with cannula 420 of primary trocar 120), a constant flow of insufflation fluid may be delivered and distributed to patient cavity 150 without much, if any, disturbance.

This disclosure recognizes that outer lumen 220 may be subdivided into one or more chambers. As an example, outer lumen 220 may be divided into two chambers—the first chamber providing a flow path for insufflation fluid, the second chamber including one or more sensors. The one or more sensors may be configured to measure and communicate information about the sensor's environment. For example, a sensor 216 positioned in the second chamber may measure information indicative of pressure inside patient cavity 150. Because second chamber is walled off from the first chamber, the flow of insufflation fluid through the first chamber does not affect the measurements taken by the pressure sensor 216 positioned within the second chamber.

Figure 3A:
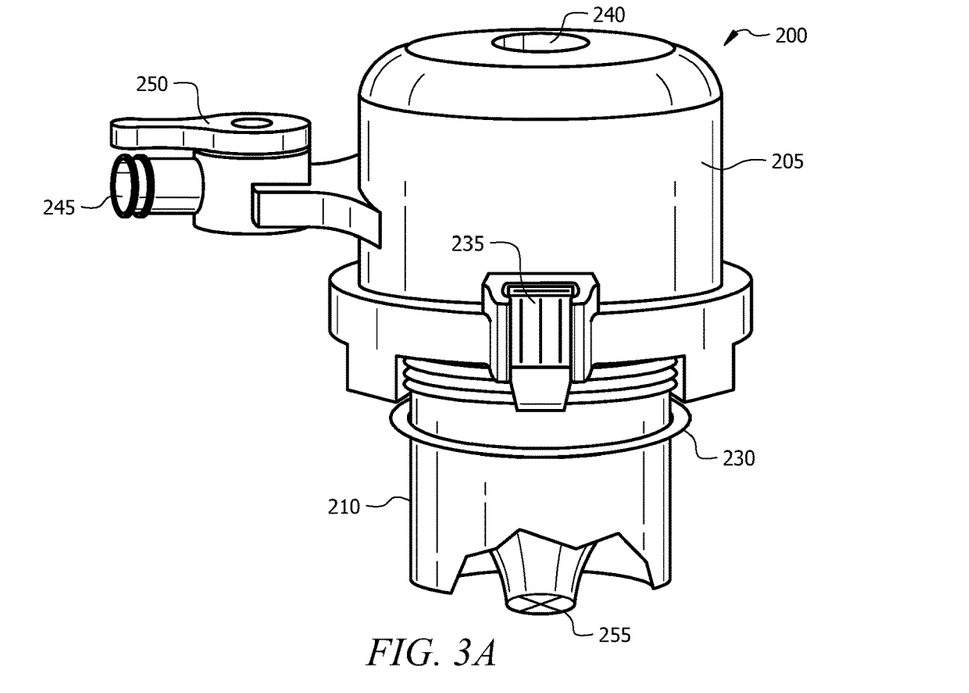
FIG. 3A is a schematic diagram of the trocar head of the secondary trocar of FIG. 2.
Figure 3B:
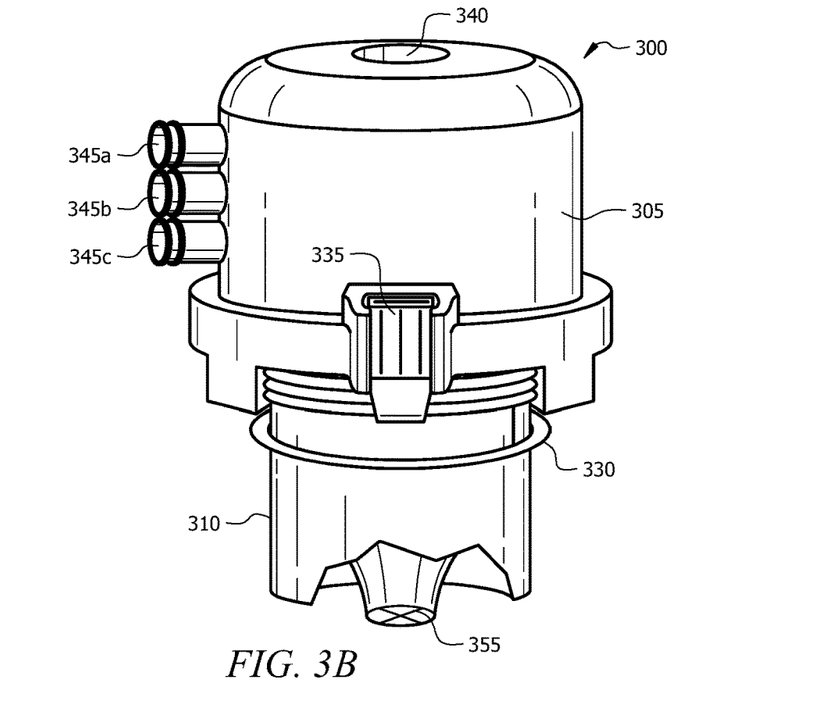
FIG. 3B is a schematic diagram of an alternative trocar head of the secondary trocar of FIG. 2.

FIGS. 3A and 3B illustrate different embodiments of trocar head and chamber of secondary trocar 110. For the avoidance of doubt, like descriptions correspond to components identified by similar numerals (e.g., the description herein of instrument opening 240 also applies to instrument opening 340 of FIG. 3; the description herein of coupling mechanism 235 also applies to instrument opening 335 of FIG. 3). Differences between these two illustrated embodiments (i.e., FIGS. 3A and 3B) include the number of intake ports 245 and the inclusion of a stopcock 250. Specifically, FIG. 3A illustrates a single intake port 245 extending from trocar head 205 and including a stopcock 250 therebetween. As discussed above, intake port 245 is configured to receive a substance (e.g., insufflation fluid) from a conduit coupled to intake port 245 and direct the insufflation fluid through trocar assembly 100. Stopcock 250 is a valve configured to control the flow of a substance (e.g., insufflation fluid) through trocar assembly 100. As one of ordinary skill in the art will understand, a flow path may be opened or closed by manipulating the position of stopcock 250. Although described and depicted as being positioned between trocar head 205 and intake port 245, stopcock 250 may be positioned at any suitable position along a substance flow path. For example, stopcock 250 may alternatively be positioned on, within or between one or more conduits coupled to intake port 245.

FIG. 3B depicts secondary trocar 300 (an alternative design to secondary trocar 200). In the depicted embodiment, trocar head 305 includes a plurality of intake ports 345, each configured to couple to one or more conduits. As discussed above, intake ports 345 may be configured to deliver one or more substances to trocar assembly 100. As an example, insufflation fluid may be delivered to intake port 345a while hydration fluid is delivered to intake port 345b. In addition to delivering substances, intake ports 345 may also serve as entry points for electrical leads (e.g., for a heater). In some embodiments, intake port 345c receives electrical leads. The electrical leads may or may not include electromagnetic sheathing. As one of ordinary skill in the art will understand, heating and/or humidifying insufflation gas immediately prior to injecting the insufflation gas into patient cavity 150 can minimize losses that would otherwise occur if insufflation gas is heated and/or humidified by an external insufflator. Although FIG. 3B is depicted without the inclusion of a stopcock 250, this disclosure recognizes that one or more stopcocks 250 may be added to secondary trocar 300 to control the flow of one or more substances being delivered to and/or from trocar assembly 100.

FIGS. 3A and 3B also show, in cut-away view, a one-way valve 255, 355 positioned within chamber 210 and 440, respectively. In some embodiments, one-way valve 255, 355 is positioned between instrument opening 240 and inner lumen 218 (e.g., in trocar head 205 and/or chamber 210). As depicted in FIGS. 3A and 3B, one-way valves 255 and 355 are positioned within chambers 210 and 440, respectively. Generally, one-way valve 255, 355 is configured to permit forward flow and prevent backflow. One-way valve 255, 355 is sized to accommodate one or more medical instruments therethrough and to create a fluid seal when the one or more medical instruments are removed via instrument opening 240. In some embodiments, one-way valve 255, 355 is a duckbill valve. One-way valve 255, 355 may be composed of any suitable material such as rubber or synthetic elastomer.

Figure 4:
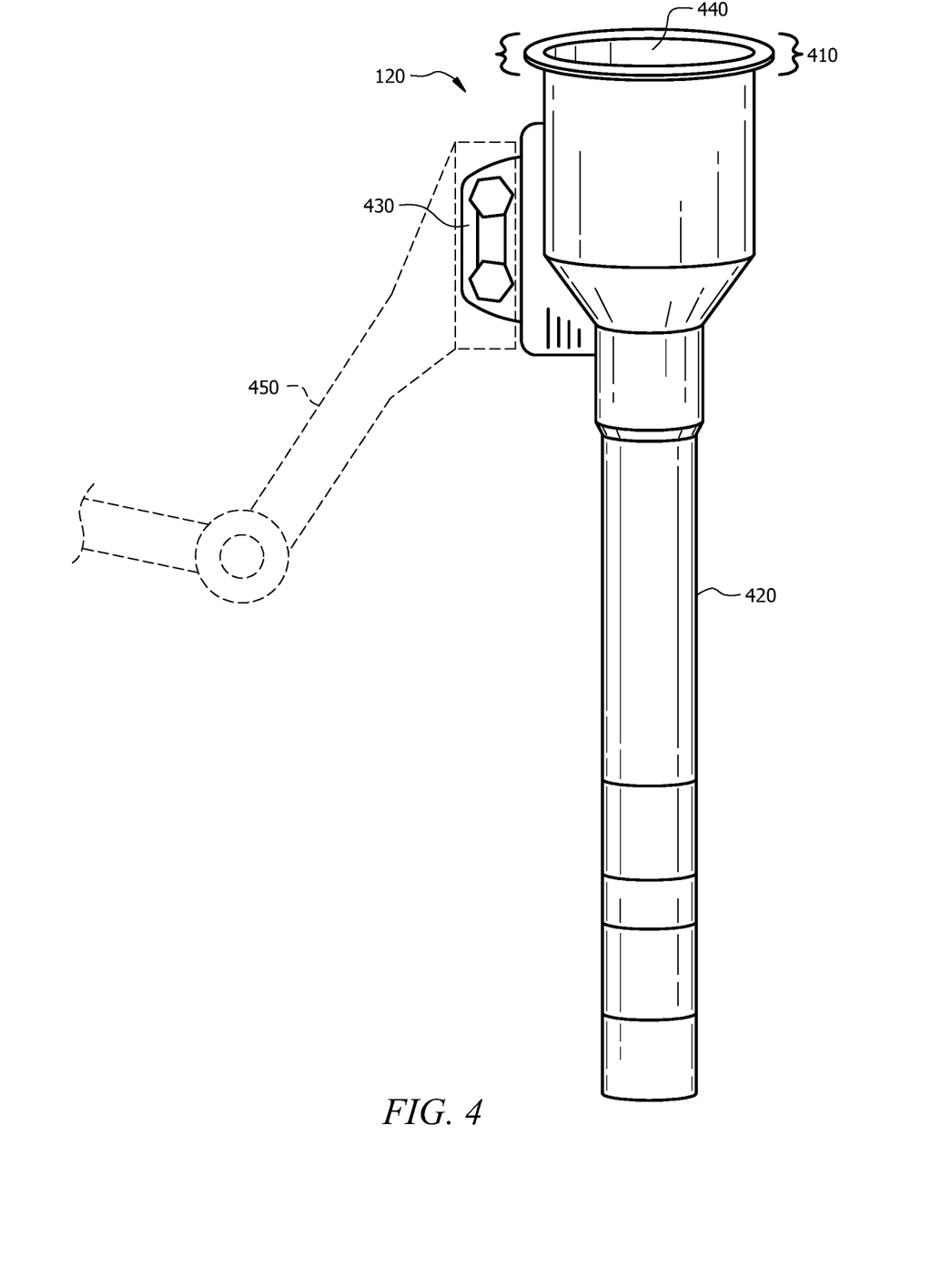
FIG. 4 is a schematic diagram of the primary trocar of FIG. 1, according to certain embodiments.

FIG. 4 illustrates an embodiment of primary trocar 120. As described above, primary trocar 120 includes a lip 410, a cannula 420, and a docking mount 430. In some embodiments, primary trocar 120 also includes a chamber 340. As discussed above, chamber 340 may be sized to accommodate chamber 210 of secondary trocar 110.

Lip 410 is configured to engage with one or more coupling mechanisms 235 of secondary trocar 110 such as to secure primary trocar 120 to secondary trocar 110. Cannula 420 is configured to accommodate cannula 215 of secondary trocar 110 therethrough. In some embodiments, a length of cannula 215 of secondary trocar is greater than a length of cannula 420. In particular embodiments, apertures 225 of secondary trocar 110 extend beyond a distal end of cannula 420, when trocar assembly 100 is assembled, to effectively deliver a substance to patient cavity 150.

Docking mount 430 is any attachment point of primary trocar 120 that is configured to couple to a surgical robot. In some embodiments, surgical robot is programmed to recognize and grasp docking mount 430 of primary trocar 120. In some embodiments, docking mount 430 is recognized and grasped by an arm of a surgical robot (shown in dashed lines and indicated by numeral 450).

Figure 5:
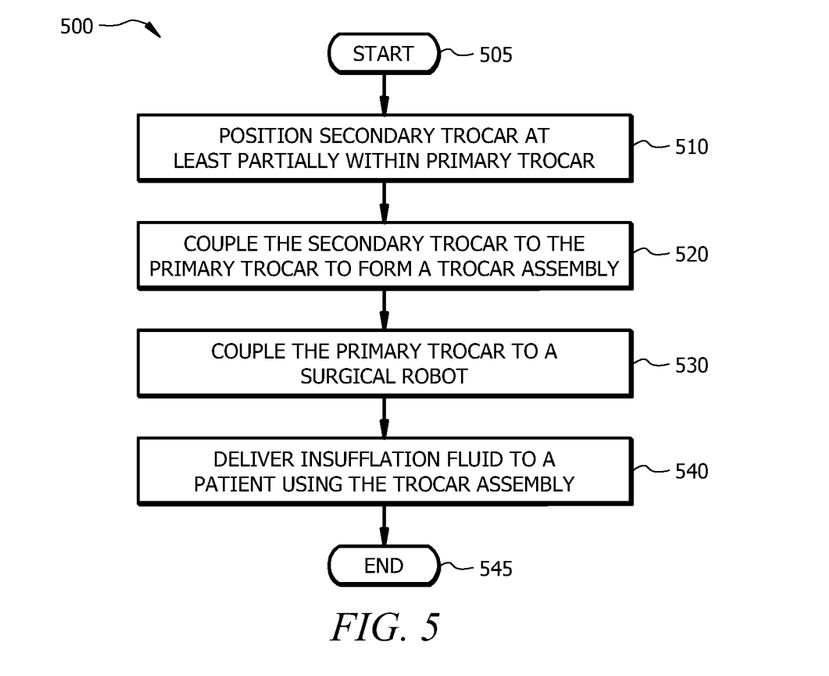
FIG. 5 is a flow chart illustrating a method for delivering insufflation fluid to a body cavity using the trocar assembly of FIG. 1.

FIG. 5 is a flowchart illustrating a method 500 of delivering insufflation fluid to patient cavity 150 using trocar assembly 100. One or more of the following steps may be performed by a medical professional such as a surgeon or surgical nurse. Method 500 may include some or all of the steps described below and can be re-ordered as necessary and/or desired. For example, although this disclosure describes and depicts step 530 being performed after step 510, this disclosure recognizes that step 530 may be performed prior to performance of step 510.

The method begins at a step 505 and continues to a step 510. At step 510, secondary trocar 110 is positioned at least partially within primary trocar 120. As an example, cannula 215 of secondary trocar 110 may be inserted through cannula 420 of primary trocar 120 such that chamber 210 of secondary trocar 110 rests inside of chamber 320 of primary trocar 120. As another example, cannula 215 of secondary trocar 110 may be inserted through cannula 420 of primary trocar 120 such that apertures 225 of secondary trocar extend beyond a distal end of cannula 420 of primary trocar. In some embodiments, secondary trocar 110 is positioned within primary trocar 120 as illustrated in FIG. 1B. Once secondary trocar 110 is positioned at least partially within primary trocar 120, the method 500 may proceed to a step 520.

At step 520, trocar assembly 100 is formed by coupling secondary trocar 110 to primary trocar 120. Coupling may performed in any suitable manner. As illustrated in FIG. 1A, coupling of secondary trocar 110 and primary trocar 120 may be performed by engaging lip 410 of primary trocar 120 with one or more coupling mechanisms 235. In some embodiments, coupling mechanisms include a depressible button that facilitates movement of latches that engage, or disengage, lip 410 of primary trocar 120. Although this disclosure recognizes benefits of coupling secondary trocar 110 to primary trocar 120 securely, such as to resist movement between secondary trocar 110 and primary trocar 120, secondary trocar 110 and primary trocar 120 can also be coupled loosely, such as to permit some movement between secondary trocar 110 and primary trocar 120. In some embodiments, a fluid seal is created between primary trocar 120 and secondary trocar 110 when coupled. The fluid seal may be at least partially created by gasket 230. Once coupled, the method 500 may proceed to a step 530.

At step 530, primary trocar 120 is coupled to a surgical robot. In some embodiments, the attachment site of primary trocar 120 and surgical robot is docking mount 430 of primary trocar 120. As discussed above, surgical robot may be programmed to recognize and grasp docking mount 430. Once the coupling of primary trocar 120 and surgical robot is complete, the surgical robot may control movement of primary trocar 120. Because, at step 530, primary trocar 120 is coupled to secondary trocar 110, movement of primary trocar 120 also results in the movement of secondary trocar 110. Accordingly, the surgical robot may be able to control the movement of trocar assembly 100. Once primary trocar 120 has been coupled to the surgical robot, the method 500 proceeds to a step 540.

At step 540, insufflation fluid is delivered to patient cavity 150 using trocar assembly 100. In some embodiments, insufflation fluid is delivered to trocar assembly 100 via a conduit coupled on one end to at least one intake port 245 and on the other end to an insufflator. Once insufflation fluid is delivered to intake port(s) 245, the insufflation fluid is directed along a flow path within trocar assembly 100 to patient cavity 150. In some embodiments, insufflation fluid follows the following flow path within trocar assembly 100: enters via intake port 245 of secondary trocar 110, directed through trocar head 205 of secondary trocar 110 to outer lumen 220 of secondary trocar 110, and exits outer lumen 220 of secondary trocar 110 via apertures 225 of secondary trocar 110.

In some embodiments, trocar assembly 100 includes one or more sensors. As an example, trocar assembly 100 may include one or more pressure sensors, temperature sensors, and/or humidity sensors. Sensors of trocar assembly 100 may be configured to sense and communicate information about the sensors' environment. The sensors may be positioned in, on, or through primary trocar 120 and/or secondary trocar 110. As one example, trocar assembly 100 may include a pressure sensor 216 located in the outer lumen 220 of secondary trocar 110. Such pressure sensor may be configured to measure a pressure indicative of the pressure of patient cavity 150. As one of ordinary skill in the art will understand, more reliable pressure measurements are taken by sensors positioned closer (in proximity) to the site of interest. Once a pressure measurement is recorded, the pressure sensor 216 may communicate the measurement to a processor (e.g., a processor of an insufflator) which uses the measurement to determine how much insufflation fluid to deliver to patient cavity 150. As another example, trocar assembly may include a primary pressure sensor (acts in accordance with description above) and a backup pressure sensor. Like the primary pressure sensor, backup pressure sensor may be configured to take measurements indicative of pressures of patient cavity 150. As described in U.S. application Ser. No. 15/610,026, filed on May 31, 2017 and entitled "Method and system for controlling pressurization of a patient cavity using a pressure sensor in a trocar," which is incorporated by reference herein, insufflation fluid may be delivered to patient cavity 150 based on the measurements taken by the backup pressure sensor in the event that readings from the primary pressure sensor are deemed unreliable. A sensor's measurements may be unreliable for any number of reasons. As one example, readings of a primary pressure sensor located within outer lumen 220 may become unreliable because apertures 225 of secondary trocar 110 become blocked.

As yet another example, trocar assembly 100 may include a humidity and/or temperature sensor within chamber 210 of secondary trocar 110. Such sensors may be configured to detect humidity and temperature information regarding the insufflation fluid being delivered to the patient cavity. Various actions may be taken in response to receiving these sensor measurements. For example, in response to receiving a temperature/humidity measurement that is lower than a particular threshold, a surgeon may manipulate certain devices or components to facilitate temperature/humidity change.

Although FIGS. 1-5 have been described above as including particular steps and/or components, the method and systems of these FIGURES may include any combination of any of the described steps and/or components and any of the options or features described herein, as would be understood by one of ordinary skill in the art. For example, any of the steps, options, or features described in reference to one figure may be utilized in combination with any number of other steps, options, or features described in reference to another figure, as would be understood by one of ordinary skill in the art.

Although the embodiments in the disclosure have been described in detail, numerous changes, substitutions, variations, alterations, and modifications may be ascertained by those skilled in the art. It is intended that the present disclosure encompass all such changes, substitutions, variations, alterations, and modifications. Additionally, one or more features described herein may be combined with one or more embodiments also described herein.

What is claimed is:

1. A system comprising:
a primary trocar comprising a lip, a single lumen, and a docking mount, the docking mount being configured to engage with a robotic arm of a surgical robot; and
a secondary trocar configured to be positioned at least partially within the primary trocar and being further configured to facilitate delivery of insufflation fluid to a patient cavity, the secondary trocar comprising:
 a trocar head comprising one or more latches configured to engage the lip of the primary trocar to facilitate coupling of the primary trocar and the secondary trocar;
 a double lumen comprising an outer lumen disposed about an inner lumen, the outer lumen comprising at least one sensor and one or more openings, the at least one sensor being configured to determine a pressure measurement indicative of a pressure of the patient cavity and the one or more openings configured to direct the insufflation fluid into the patient cavity; and
 one or more conditioning elements configured to heat and/or humidify the insufflation fluid;
wherein, when the primary trocar and the secondary trocar are coupled:
 a fluid seal exists between the primary trocar and the secondary trocar, the fluid seal being provided at least partially by a gasket;
 the one or more openings in the outer lumen of the secondary trocar extend beyond the single lumen of the primary trocar; and
 the insufflation fluid is supplied based on the pressure measurement.

2. A system comprising:
a primary trocar comprising a lip, a single lumen, and a docking mount, the docking mount projecting radially outward from a head of the primary trocar and being configured to engage with a robotic arm of a surgical robot; and
a secondary trocar configured to be positioned at least partially within the primary trocar and being further configured to facilitate delivery of insufflation fluid to a patient cavity, the secondary trocar comprising:
 a trocar head; and
 a double lumen comprising an outer lumen disposed about an inner lumen, the outer lumen comprising one or more openings configured to direct the insufflation fluid into the patient cavity;
wherein:
 the trocar head comprises one or more latches configured to engage the lip of the primary trocar to facilitate coupling of the primary trocar and the secondary trocar; and
 when the primary trocar and the secondary trocar are coupled:
  a fluid seal exists between the primary trocar and the secondary trocar; and
  the one or more openings in the outer lumen of the secondary trocar extend beyond the single lumen of the primary trocar.

3. The system of claim 2, wherein the secondary trocar further comprises one or more conditioning elements configured to heat and/or humidify the insufflation fluid.

4. The system of claim 2, wherein:
the fluid seal between the primary trocar and the secondary trocar is at least partially provided by a gasket.

5. The system of claim 2, wherein the trocar head of the secondary trocar further comprises a stopcock configured to open or close to permit or restrict, respectively, a flow of the insufflation fluid.

6. The system of claim 2, wherein the outer lumen of the secondary trocar abuts the single lumen of the primary trocar when the primary trocar and the secondary trocar are coupled.

7. The system of claim 2, wherein the inner lumen of the secondary trocar is sized to accommodate a medical instrument therethrough.

8. The system of claim 2, wherein the secondary trocar further comprises an instrument opening and a one-way valve, the one-way valve configured to provide a fluid seal when a medical instrument is not present within the inner lumen of the secondary trocar.

9. The system of claim 8, wherein the one-way valve is a duckbill valve.

10. The system of claim 2, wherein the trocar head further comprises at least one intake port configured to receive, via a conduit, the insufflation fluid from an insufflator.

11. The system of claim 2, further comprising:
an insufflator configured to supply the insufflation fluid to the patient cavity, the insufflator comprising a processor and a computer readable media having logic stored thereon; and
at least one pressure sensor communicatively coupled to the insufflator, the at least one pressure sensor configured to:
determine a pressure measurement indicative of a pressure of the patient cavity;
communicate the pressure measurement to the insufflator;
wherein the logic stored on the computer readable media is configured, when executed on the processor, to control the supply of the insufflation fluid to the patient cavity based on the pressure measurement from the at least one pressure sensor.

12. The system of claim 11, wherein the at least one pressure sensor is positioned on, in, or through at least one of the primary trocar or the secondary trocar.

* * * * *